US007482591B2

United States Patent
Herrington et al.

(10) Patent No.: US 7,482,591 B2
(45) Date of Patent: Jan. 27, 2009

(54) CARBONATE SCALE DETECTOR

(75) Inventors: Rodney E. Herrington, Albuquerque, NM (US); Curtis Mitchke, Albuquerque, NM (US)

(73) Assignee: MIOX Corporation, Albuquerque, NM (US)

( * ) Notice: Subject to any disclaimer, the term of this patent is extended or adjusted under 35 U.S.C. 154(b) by 369 days.

(21) Appl. No.: 10/946,658

(22) Filed: Sep. 22, 2004

(65) Prior Publication Data

US 2006/0060787 A1 Mar. 23, 2006

(51) Int. Cl.
*G01J 5/02* (2006.01)
*G01J 1/42* (2006.01)

(52) U.S. Cl. .................................. 250/343; 250/373
(58) Field of Classification Search ............... 250/343, 250/345, 356.1, 373, 459.1; 600/532
See application file for complete search history.

(56) References Cited

U.S. PATENT DOCUMENTS

| | | | | |
|---|---|---|---|---|
| 4,210,809 | A * | 7/1980 | Pelavin ........................ 250/343 |
| 4,462,962 | A * | 7/1984 | Baba et al. ..................... 422/58 |
| 4,746,218 | A * | 5/1988 | Lord, III ...................... 356/437 |
| 4,761,208 | A * | 8/1988 | Gram et al. .................. 210/748 |
| 4,775,794 | A * | 10/1988 | Behmann .................... 250/373 |
| 4,912,332 | A * | 3/1990 | Siebel et al. ............. 250/356.1 |
| 5,304,492 | A * | 4/1994 | Klinkhammer ............... 436/52 |
| 5,320,718 | A * | 6/1994 | Molter et al. ................ 205/555 |
| 5,420,432 | A * | 5/1995 | Manook et al. .............. 250/373 |
| 5,795,459 | A * | 8/1998 | Sweeney ..................... 205/701 |
| 5,864,140 | A | 1/1999 | Owens |
| 5,957,858 | A | 9/1999 | Micheels et al. |
| 6,037,592 | A * | 3/2000 | Sunshine et al. ............ 250/343 |
| 6,180,014 | B1 * | 1/2001 | Salama ........................ 210/748 |
| 6,525,325 | B1 * | 2/2003 | Andrews et al. ......... 250/461.1 |
| 6,736,966 | B2 * | 5/2004 | Herrington et al. .......... 210/192 |
| 6,880,402 | B1 * | 4/2005 | Couet et al. .................... 73/579 |
| 6,943,358 | B1 * | 9/2005 | Andrews et al. ......... 250/459.1 |
| 7,175,715 | B2 * | 2/2007 | Eiermann .................... 134/10 |
| 2004/0135980 | A1 | 7/2004 | Manz et al. |

* cited by examiner

*Primary Examiner*—David P Porta
*Assistant Examiner*—Faye Boosalis
(74) *Attorney, Agent, or Firm*—Deborah A. Peacock; Philip D. Askenazy; Peacock Myers, P.C.

(57) ABSTRACT

An apparatus and method for detecting carbonate scale. An energy emitting device transmits energy through one optical window, through a fluid stream, and out through a second optical window where the energy is detected by an energy receiving device. As scale, such as that due to carbonate present in the fluid, accumulates on the wetted surface of the optical windows, the transmission of the energy through the optical windows is obscured. The optical windows may optionally be coated and electrically charged to promote the formation of carbonate scale on the wetted surface of the window. The optical windows can be cleaned by reversing their polarity. By correlating the rate of energy intensity reduction to carbonate scale formation, the concentration of carbonate in the fluid stream can be determined. The carbonate detector can be used to alarm, shutdown, or control operation of equipment that may be adversely affected by the presence of carbonate in the fluid stream.

50 Claims, 4 Drawing Sheets

Plan View in Section

Side View

Plan View in Section

Side View

Plan View in Section

CARBONATE SCALE DETECTOR

FIELD OF THE INVENTION

This invention relates to a method and device for measuring the presence of carbonate scale in a fluid stream.

BACKGROUND OF THE INVENTION

Electrolytic cells are used in a variety of applications to generate oxidants for use in disinfection. Electrolytic technologies have been developed to produce mixed-oxidants and sodium hypochlorite solutions from a sodium chloride brine solution. U.S. Pat. No. 4,761,208 by Gram, et al. describes an electrolytic method and cell for sterilizing water. These electrolytic cells typically have a source water feed stream and a brine feed stream. The feed water can typically be softened to remove carbonate from the water stream, and softened water can also be used to generate the brine solution. However, salt for making brine often contains calcium as a contaminant in the salt. Due to the concentration of the brine, the brine can not be softened using ion exchange resin.

Operating conditions within the cell are ideal for the formation of scale deposits on electrode plates. For instance, calcium carbonate scale can build up on the cathode electrode of a chlorine producing electrolytic brine cell. Carbonate scale can electrically blind the cathode causing localized current density increases in the opposing dimensionally stable anode (DSA), which can cause passivation failure of the DSA coating. This failure mode can cause rapid destruction of the electrolytic cell.

By measuring the formation of carbonate in the oxidant fluid stream exiting the electrolytic cell, the electrolytic cell operation can be alarmed or terminated. This will allow maintenance to be timely performed on the electrolytic cell to repair the effects of the carbonate scale before destruction of the electrolytic cell occurs. The present invention can also be used to detect carbonate formation in any aqueous fluid where carbonate formation is considered a contaminant in the system. Examples include boiler water systems, distilling systems, ion exchange water softening to indicate that resin regeneration is required, membrane softening systems, dialysis systems, commercial sodium hypochlorite pumping and piping systems, and any other applications where a contaminant attracted to a material in a high pH environment can be detected.

SUMMARY OF THE INVENTION

The present invention is an apparatus to detect scale formation in a fluid stream. The apparatus comprises a flow-through chamber for the fluid stream; at least two optical windows, at least one of the optical windows accumulating scale formation from the fluid stream; an energy emitting device transmitting an energy beam through both the optical windows and the fluid stream; and an energy receiving device measuring the intensity of the energy beam. The energy emitting device preferably comprises an infrared LED, and the energy receiving device preferably comprises an infrared phototransistor. The optical windows preferably comprise quartz or synthetic sapphire.

The apparatus preferably further comprises a control system for receiving a signal from the energy receiving device, wherein the signal is preferably correlated to the intensity, which is preferably related to the amount of the scale formation. The control system is preferably activated when the intensity reaches a level indicating a predetermined amount of scale formation. The rate of change of the signal preferably determines a concentration of carbonate in the fluid stream. The control system preferably comprises a circuit for quantifying the level of scale in the fluid stream, and preferably comprises an adjustable control mechanism providing adjustment for detection sensitivity. The control system further preferably comprises a switch for transmitting a signal to an external device, and preferably comprises a device such as an alarm, electrolytic cell controller, ion exchange controller, or reversible power supply. The electrolytic cell controller preferably deactivates a power supply for an electrolytic cell and initiates a cleaning cycle. The ion exchange controller preferably initiates regeneration of ion exchange resin.

The present invention is preferably used to detect and control scale formation in electrolytic cell applications and is useful for detecting carbonate scale formation, controlling regeneration cycles in ion exchange resin systems, and detecting and controlling scale formation in a system where scale formation is detrimental to system operation. Such a system includes but is not limited to an electrolytic chlorine cell, an electrolytic device, a boiler water system, a distiller, a water softening system, or a membrane system.

Each of the optical windows of the present invention preferably comprises a coating, which preferably comprises at least one property of, including but not limited to, electrically conductive, optically transparent, chemically resistant, chemically inert, electrolytically active, metallic, and combinations thereof. The coating preferably comprises a titanium thin film or a diamond coating. One of the optical windows preferably comprises an anode and at least one other of the optical windows preferably comprises a cathode. The apparatus preferably further comprises a power supply providing a positive electrical potential to the anode and a negative electrical potential to the cathode. The electrical polarity of the anode and the cathode is preferably reversible. Reversing the polarity preferably cleans a surface of the cathode, preferably by dissolving the scale formation.

The apparatus optionally further comprises an anode which preferably comprises a dimensionally stable anode. In this embodiment the optical windows preferably comprise cathodes. The apparatus preferably further comprises a reversible power supply providing a positive electrical potential to the anode and a negative electrical potential to the cathode.

The present invention is also a method for detecting scale formation, the method comprising: shining an energy beam, preferably comprising infrared energy, through a first optical window, through a fluid stream, and through a second optical window; detecting the intensity of the energy beam; and correlating the intensity with the amount of scale formation on at least one of the optical windows. The method preferably further comprises determining the concentration of carbonate in the fluid stream, preferably by measuring the rate of change of the intensity. The method preferably further comprises activating a control system when a predetermined amount of scale formation is detected. The method optionally comprises any of the steps of alerting an operator, stopping operation of a system, cleaning the system, and/or initiating regeneration of ion exchange resin in a water softening system.

Each of the optical windows preferably comprises a coating, in which case the method preferably comprises applying a positive electrical potential to one of the optical windows and applying a negative electrical potential to the other optical window. Scale on at least one of the optical windows is optionally dissolved, preferably by reversing the polarity of the optical windows or flushing the at least one optical window with an acid.

The method optionally comprises providing an anode, which preferably comprises a third coated optical window or a dimensionally stable anode. The method preferably comprises applying a positive electrical potential to the anode and applying a negative electrical potential to the first and second optical windows. The first and second optical windows are preferably cleaned by applying a negative electrical potential to the anode and applying a positive electrical potential to the first and second optical windows.

An object of the present invention is to provide a solid state means of detecting or measuring the rate of carbonate scale formation in an aqueous stream.

Another object of the present invention is that it may be used in any aqueous-containing systems where carbonate formation is detrimental to operation of the system, including but not limited to applications such as electrolytic chlorine cells, other electrolytic devices, boiler water systems, distillers, water softening systems, and membrane systems.

A primary advantage of the present invention is that the detector is solid state and thus can be manufactured at low cost and is small in size.

Another advantage of the present invention is that, unlike conventional systems, it does not require the use of chemical reagents for detecting carbonate in the aqueous stream or for cleaning the carbonate detector.

A further advantage of the present invention is that it may be cleaned by reversing the electrical polarity of the optical windows.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DETAILED DESCRIPTION OF THE INVENTION

Figure 1A:
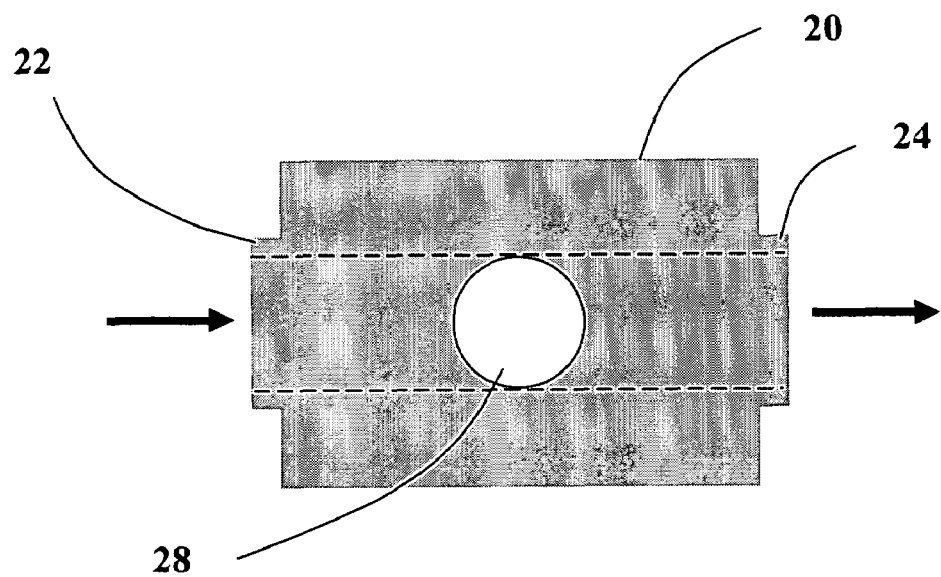
FIGS. 1a and 1b are diagrams of the preferred embodiment of the present invention with two optical windows.
Figure 1B:
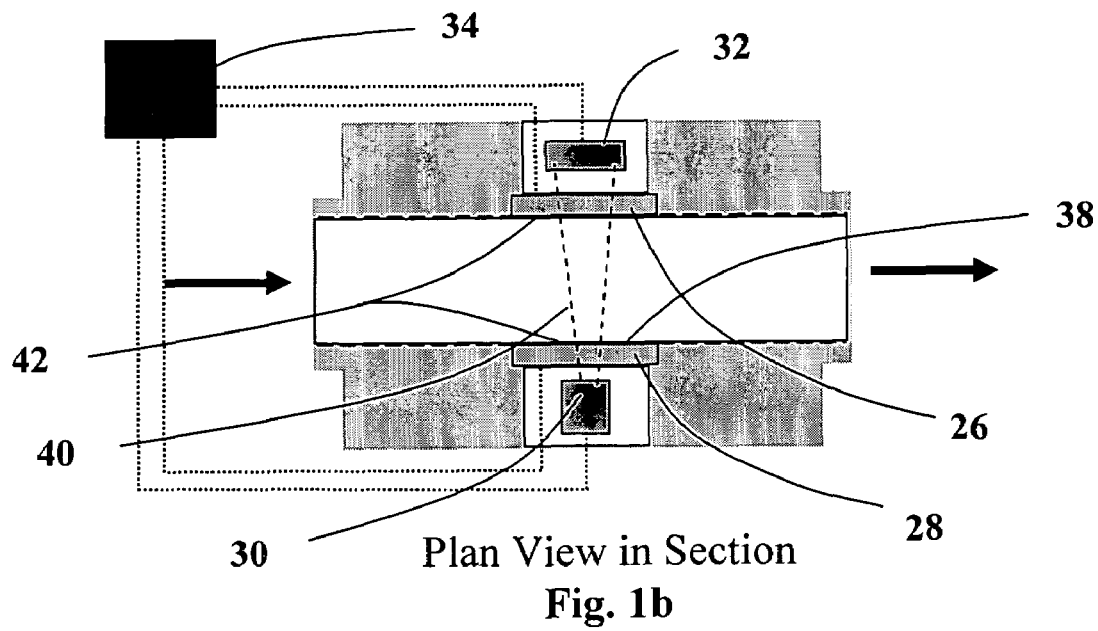

A preferred embodiment of the present invention, depicted in FIGS. 1a and 1b, comprises fluid flow through chamber 20 comprising inlet port 22 and outlet port 24. The fluid optionally comprises electrolyte or one or more oxidants. Optical windows 26 and 28, which are preferably tangent to the fluid flow, allow transmission of energy through the fluid flowing within chamber 20. Optical windows 26 and 28 are sealed to or disposed on chamber 20 and fluid flowing within chamber 20 is in wetted contact with the inside surface of optical windows 26 and 28. Optical windows 26, 28 preferably comprise, quartz, synthetic sapphire, or any other material compatible with the aqueous fluid. Quartz and synthetic sapphire have excellent chemical resistance to high chlorine concentrations.

In the preferred embodiment, energy emitting device 30, comprising for example an infrared emitter such as an LED, shines energy beam 40 through optical window 28, then through the aqueous solution, and finally through opposing optical window 26 and on to energy receiving device 32, preferably an infrared phototransistor. An electrical signal generated by energy receiving device 32 is preferably transmitted to control board or system 34. The intensity of energy received at energy receiving device 32 preferably determines whether control board 34 activates a switch for ultimate transmission to the system to be controlled. As carbonate or other contamination accumulates on the wetted surface of optical windows 26, 28 the transmission of energy through them is obscured. The reduction in energy transmission can be used as an indicator to determine that carbonate as a contaminant is present in the fluid stream. Control board 34 preferably comprises a circuit or other means for quantifying the level of scale both on optical windows 26, 28 and in the fluid stream.

The rate of degradation of the optical path due to blockage of either or both optical windows 26, 28, i.e. the rate of carbonate formation or deposition, is correlated with the concentration of carbonate in the aqueous fluid. In this way, the concentration of carbonate in the aqueous path is determined. This is useful information for water quality analysis or when the present apparatus is used as a fluid quality indicator.

In a preferred embodiment of the present invention, anode optical window 26 is preferably coated with film 42, which preferably comprises diamond or alternatively a thin metal layer comprising, for example but not limited to, titanium. Film 42 is preferably applied by chemical vapor deposition, sputtering, physical vapor deposition, evaporation, or any other method known in the art for depositing a film on a substrate. Anode optical window 26 is located within the fluid stream flowing within chamber 20 and is opposite optical window 28, which acts as a cathode. Optical window 28 is also preferably coated with film 42 (preferably diamond). The films (preferably diamond) preferably are electrically conductive, optically transparent, electrolytically active, and/or have excellent chemical resistance or are chemically inert. Diamond has excellent chemical resistance to a wide variety of chemicals.

A power supply preferably applies a positive direct current electrical potential to film 42 on anode optical window 26 and a negative electrical potential to film 42 deposited on cathode optical window 28. The potentials may optionally be reversed. Total dissolved solids (TDS) within the fluid solution flowing within chamber 20 provide the electrical conduction path between film 42 on anode optical window 26 and film 42 on cathode optical window 28. The applied current creates an electrolytic reaction, thus facilitating carbonate formation on optical window 28. High pH conditions at film 42 deposited on cathode optical window 28 attracts carbonate from the fluid solution to deposit carbonate film 38 on cathode optical window 28.

Carbonate scale typically forms on the cathode element of an electrolytic cell which is associated with high pH conditions. This feature is utilized to generate a high pH condition on cathode optical window 28 in order to accelerate the deposition of carbonate scale. With a negative charge applied to the titanium metal or diamond deposited on cathode optical window 28, it acts as a cathode for attraction of carbonate that may be in the fluid stream. As carbonate scale forms on cathode optical window 28, energy transmission, preferably infrared, is blocked. The loss of energy transmission due to carbonate blockage is detected, indicating not only that carbonate formation is evident within the detector, but more importantly that carbonate is present in the fluid-containing system.

In the preferred embodiment of the present invention, the carbonate detection apparatus can be cleaned by reversing the polarity of the anode and cathode in the detector. This method for scale removal is described in U.S. Pat. No. 4,088,550 to Malkin, entitled "Periodic Removal of Cathodic Deposits by Intermittent Reversal of the Polarity of the Cathodes", incorporated herein by reference. In this way, the cathodes are now the anode, and the low pH condition at the anode removes the carbonate scale. In an alternative embodiment, the carbonate detector, particularly the cathode, can be easily cleaned of carbonate scale by flushing the device with an appropriate acid such as hydrochloric acid, acetic acid (vinegar) or other suitable compositions. For the device described herein, carbonate film 38 on optical window 28 is preferably cleaned by reversing the electrical polarity of film 42 on anode optical window 26 and film 42 on cathode optical window 28. In this manner, a low pH condition is established at cathode optical window 28 (now acting as the anode), which dissolves the carbonate formation.

Figure 2A:
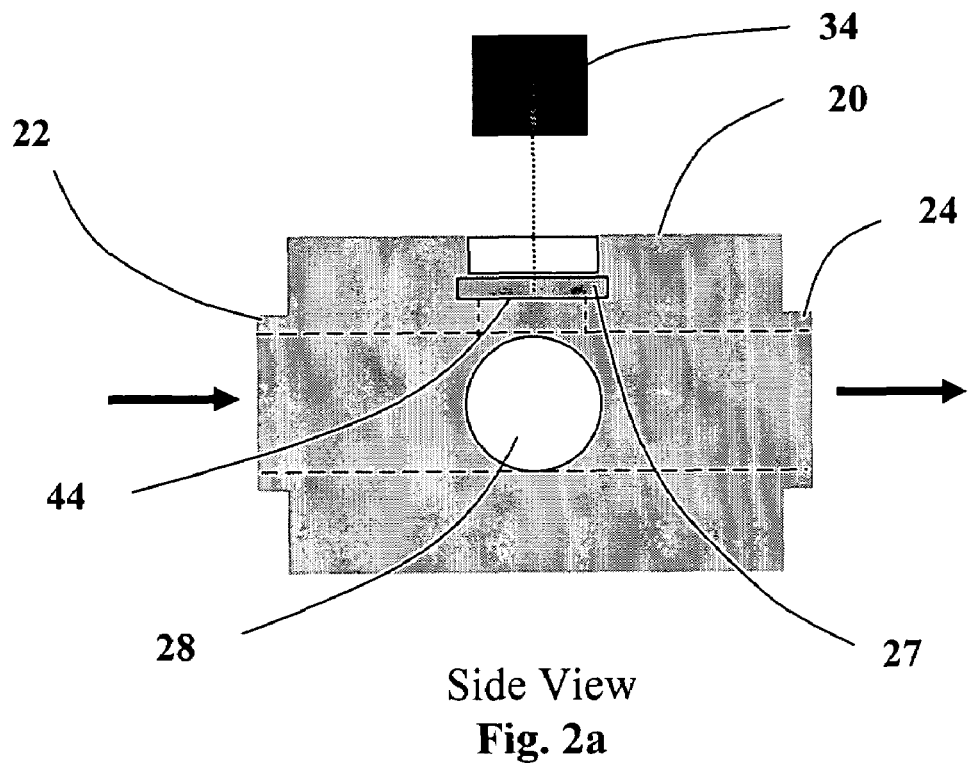
FIGS. 2a and 2b are diagrams of an alternative embodiment of the present invention with three optical windows.
Figure 2B:
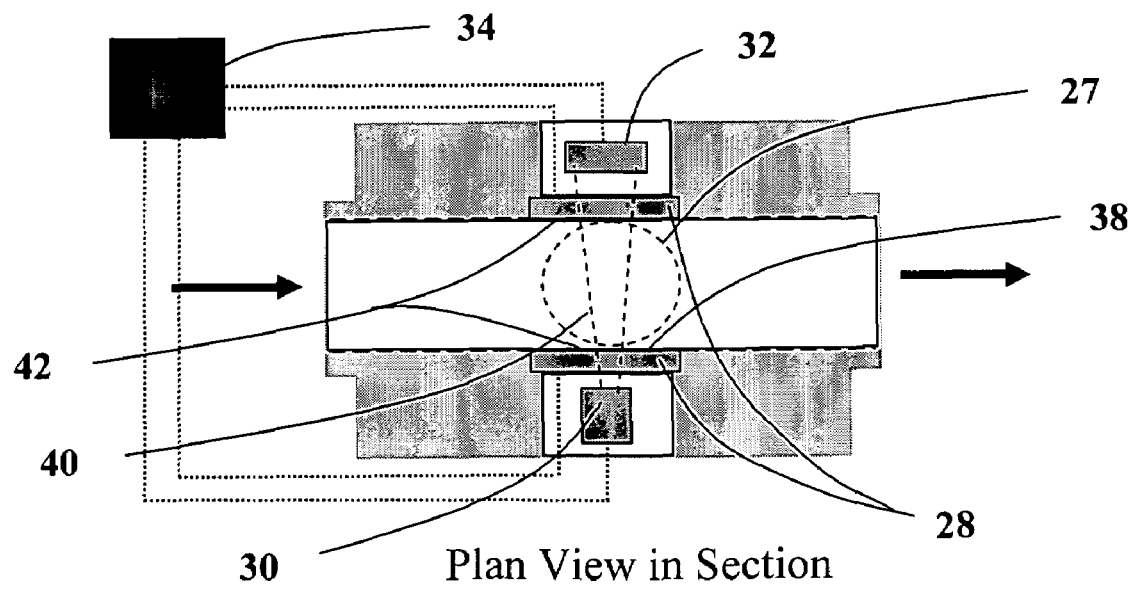

An alternative embodiment of the present invention for facilitating scale formation is shown in FIGS. 2a and 2b. Optical windows 28 allow transmission of energy through the fluid flowing within chamber 20. Optical windows 28 are sealed to chamber 20 and fluid flowing within chamber 20 is in wetted contact with the inside surface of optical windows 28. Energy emitting device 30, for example an infrared emitter LED, shines energy beam 40 through optical window 28, then through the aqueous solution, and finally through opposing optical window 28 and on to energy receiving device 32.

In this alternative embodiment of the present invention, a third window, anode optical window 27, is preferably coated with film 44 (preferably diamond). Film 44 is preferably applied by chemical vapor deposition or a similar method. Anode optical window 27 is located within the fluid stream flowing within chamber 20 and is preferably adjacent to or nearby optical windows 28, which in this embodiment both act as cathodes. Optical windows 28 are preferably coated with films 42 (preferably diamond). A positive direct current electrical potential is applied to film 44 on anode optical window 27 and negative electrical potential is applied to films 42 deposited on optical windows 28. Total dissolved solids (TDS) ore electrolyte within the fluid solution flowing within chamber 20 provide the electrical conduction path between film 44 on anode optical window 27 and films 42 on optical windows 28. The applied current creates an electrolytic reaction. High pH conditions at film 42 acting as the cathode attracts carbonate from the fluid solution to deposit carbonate film 38 on optical windows 28.

Anode optical window 27 may alternatively be replaced by a dimensionally stable anode. Dimensionally stable anodes are described in U.S. Pat. No. 3,234,110 to Beer, entitled "Electrode and Method of Making Same," incorporated herein by reference, whereby a noble metal coating is applied over a titanium substrate. The dimensionally stable anode is preferably coated with diamond, since it is known in the art that diamond coated electrodes offer significant improvements in durability over conventional dimensionally stable anodes.

In any of the above embodiments, the electrical signal from energy receiving device 32 is preferably received at control board 34, which preferably comprises a processor or computer. The electrical signal received at control board 34, which is preferably correlated to the intensity of energy detected by energy receiving device 32, is preferably an analog signal, although it can be a digital signal. As the energy intensity detected by energy receiving device 32 decreases to a prescribed value, which preferably indicates that a substantial amount of carbonate has formed on cathode optical window 28, control board 34 preferably closes or activates a switch or relay which preferably sends a signal to the system control device to either shut down the equipment or notify the operator, preferably via an alarm, that maintenance is required to mitigate the effects of carbonate in the system. Thus operation of the equipment may be shut down or controlled to prevent carbonate in the fluid stream from damaging the equipment.

The switch closure set point can be adjusted to match the specific application. For example, a switch closure to indicate that a water softener ion exchange resin column has been saturated may be set at a very low threshold. In an electrolytic cell application, the switch threshold may be set at a higher value. In addition, the detection sensitivity of the control system is preferably adjustable. Some level of carbonate formation in the electrolytic cell may not be damaging, but a continued buildup of carbonate in the electrolytic cell will bridge the gap between anode and cathode electrodes in the electrolytic cell and begin to damage the electrolytic cell.

Control board 34 preferably evaluates the rate of carbonate buildup on cathode optical window 28 over time. The rate of carbonate buildup can be correlated to the concentration of carbonate in the aqueous fluid stream. This information is useful for fluid quality analysis or determining the effectiveness of carbonate removal systems.

Figure 3:
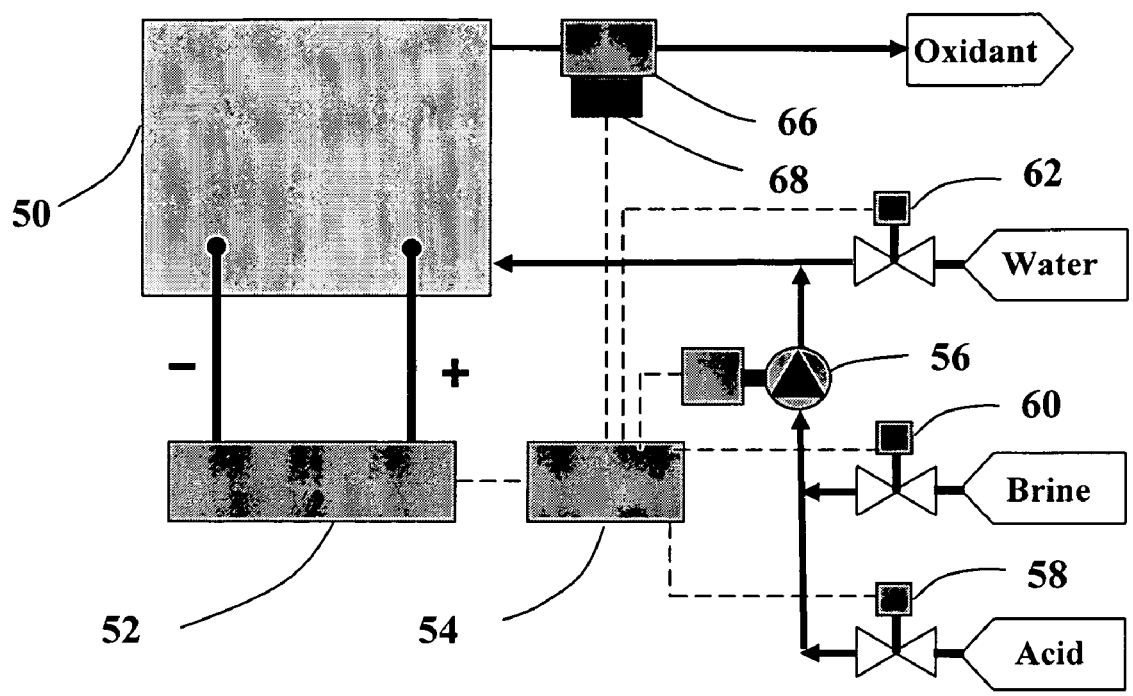
FIG. 3 is a diagram showing how the carbonate detector of the present invention is integrated into an electrolytic cell system.

FIG. 3 depicts the carbonate detector of the present invention integrated into an electrolytic cell system. Electrolytic cell 50 preferably uses dimensionally stable anodes and cathodes to convert a dilute brine solution to chlorine-based aqueous oxidants which are used to disinfect drinking water, or wastewater for cooling towers, swimming pools, and other applications requiring a chlorine or mixed oxidant disinfectant. Power to the electrodes in electrolytic cell 50 is provided by power supply 52. Water, preferably softened, is applied to electrolytic cell 50 via valve 62. Concentrated brine is fed to electrolytic cell 50 via valve 60 and is preferably metered to electrolytic cell 50 via brine pump 56. The system is preferably controlled by electrolytic cell controller 54.

Calcium as a contaminant can enter electrolytic cell 50 via the water or the brine source. Prior to entrance to electrolytic cell 50, calcium contaminants in the water source are preferably removed with an ion exchange softener or membrane softening system. However, the quality of salt used to generate the concentrated brine source varies from location to location. Brine is the primary source of calcium contaminant within electrolytic cell 50. Due to the concentration of sodium chloride in concentrated brine, neither an ion exchange softener nor a membrane softening system can effectively remove calcium contaminants from the brine solution. Because the quality of salt varies by application, the rate of carbonate formation within electrolytic cell 50 is indeterminate. As carbonate forms on electrodes within electrolytic cell 50, carbonate also forms within carbonate detector 66. When a preset value of carbonate within carbonate detector 66 is reached, carbonate detector controller 68 preferably activates a relay which preferably sends an electrical signal to electrolytic cell controller 54.

During operation of electrolytic cell 50, two phase flow in the oxidant discharge stream can create instability within energy receiving device 32 (FIG. 1). To mitigate the instability, measurement of carbonate formation can occur during the shutdown sequence from operation of electrolytic cell 50. During the shutdown sequence, power supply 52 is de-activated while water continues to flow by virtue of valve 62 remaining in the open position during the evaluation sequence of carbonate detector 66. If carbonate contamination reaches a threshold value in carbonate detector 66, carbonate detector controller 68 sends the appropriate electrical signal to electrolytic cell controller 54. Electrolytic cell controller 54 then completes the shutdown sequence of electrolytic cell 50 by closing electric valve 62. In the preferred embodiment, electrolytic cell controller 54 then activates a cleaning cycle. A preferred cleaning cycle begins by opening electric valve 58. Brine pump 56 is then activated to pump acid solution through electrolytic cell 50, out the discharge port of electrolytic cell 50 and through carbonate detector 66, thereby cleaning carbonate detector 66 and electrolytic cell 50. After the cleaning cycle is completed, electric valve 62 can be opened to purge electrolytic cell 50 with water. Carbonate detector 66 can then be activated to verify that the system is clean. Because carbonate detector 66 is downstream from electrolytic cell 50, carbonate detector 66 should be the last item cleaned.

Alternatively, carbonate detector 66 activates the relay in carbonate detector controller 68 which then sends a control signal to electrolytic cell controller 54. Electrolytic cell controller 54 then sends an alarm signal to notify the operator that maintenance is required, rather than activating an automatic acid washing sequence.

The monitoring, control, and cleaning sequence described herein can be applied to a variety of systems that are subject to carbonate contamination. For instance, a boiler or distiller water system can be monitored and alarmed in the same fashion. However, an acid washing cycle may not be the preferred cleaning sequence. To clean carbonate detector 66, carbonate detector controller 68 may alternatively reverse the polarity of the anode optical window 26 and cathode optical window 28 (FIG. 1) either by manual or automatic means, thereby cleaning carbonate from cathode optical window 28. Normal operation of carbonate detector 66 can then proceed. Similarly, the polarity of power supply 52 may be reversed in order to clean the cathode of electrolytic cell 50.

Figure 4:
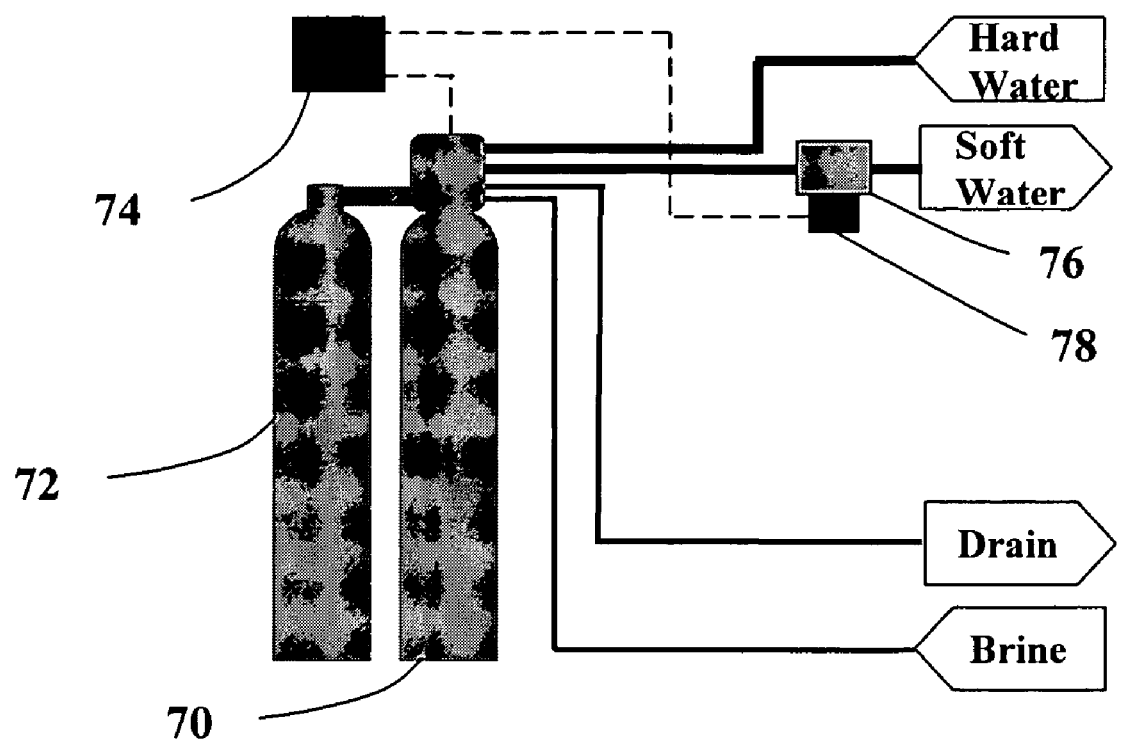
FIG. 4 is a diagram showing how the carbonate detector of the present invention is integrated into a water softening system.

In the embodiment of the present invention depicted in FIG. 4, carbonate detector 76 acts as a signaling device for regeneration of an ion exchange softening system. The ion exchange softening system comprises primary ion exchange tank 70, secondary ion exchange tank 72, and ion exchange controller 74. As the ion exchange resin in primary ion exchange tank 70 becomes saturated with calcium carbonate, the ion exchange resin can no longer attract calcium carbonate in the water stream. Carbonate then begins to form in carbonate detector 76. A signal in carbonate detector controller 78 activates a relay which is then transmitted to ion exchange controller 74. Ion exchange controller 74 then activates the regeneration cycle. In the regeneration cycle, water flow is diverted to secondary ion exchange tank 72 and primary ion exchange tank 70 is placed in the backwash cycle where the resin is purged of calcium, and the ion exchange resin is re-loaded with sodium. The cycle is repeated when secondary ion exchange tank 72 becomes saturated with calcium carbonate. Since acid cleaning cannot be utilized in this system, carbonate detector 76 is cleaned simultaneously when ion exchange controller 74 places the ion exchange system in regeneration. Carbonate detector 76 is cleaned preferably when carbonate detector controller 78 reverses polarity on the anode and cathode windows in carbonate detector 76.

Although the invention has been described in particular as to carbonate and carbonate scale detection, the invention is useful for detecting other components or contaminants and the term "scale" is used herein to describe all such materials and deposits.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all patents and publications cited above are hereby incorporated by reference.

What is claimed is:

1. An apparatus to detect scale formation in a fluid stream, said apparatus comprising:
   a flow-through chamber for the fluid stream;
   at least two optical windows comprising an electrically conductive coating, at least one of said optical windows functioning as a cathode and accumulating scale formation from the fluid stream;
   an energy emitting device transmitting an energy beam through both said optical windows and the fluid stream; and
   an energy receiving device for measuring an intensity of said energy beam; and
   a processor for correlating said intensity with an amount of said scale formation.

2. The apparatus of claim 1 wherein said energy emitting device comprises an infrared LED.

3. The apparatus of claim 1 wherein said energy receiving device comprises an infrared phototransistor.

4. The apparatus of claim 1 wherein at least one of said optical windows comprises a material selected from the group consisting of quartz and synthetic sapphire.

5. The apparatus of claim 1 comprising a control system comprising said processor for receiving a signal from said energy receiving device.

6. The apparatus of claim 5 wherein said signal is correlated to said intensity.

7. The apparatus of claim 6 wherein said control system is activated when said intensity reaches a level indicating a predetermined amount of scale formation.

8. The apparatus of claim 5 wherein a rate of change of said signal determines a concentration of carbonate in the fluid stream.

9. The apparatus of claim 5 wherein said control system comprises a circuit for quantifying a level of scale in the fluid stream.

10. The apparatus of claim 5 wherein said control system comprises an adjustable control mechanism providing adjustment for detection sensitivity.

11. The apparatus of claim 5 wherein said control system comprises a switch for transmitting a signal to an external device.

12. The apparatus of claim 5 wherein said control system comprises a device selected from the group consisting of an alarm, an electrolytic cell controller, an ion exchange controller, and a reversible power supply.

13. The apparatus of claim 12 wherein said device comprises an electrolytic cell controller and said electrolytic cell controller deactivates a power supply for an electrolytic cell and initiates a cleaning cycle.

14. The apparatus of claim 12 wherein said device comprises an ion exchange controller and said ion exchange controller initiates regeneration of ion exchange resin.

15. The apparatus of claim 1 used to detect and control scale formation in electrolytic cell applications.

16. The apparatus of claim 1 useful for detecting carbonate scale formation.

17. The apparatus of claim 1 useful to control regeneration cycles in ion exchange resin systems.

18. The apparatus of claim 1 useful to detect and control scale formation in a system where scale formation is detrimental to system operation.

19. The apparatus of claim 18 wherein said system is selected from the group consisting of an electrolytic chlorine cell, an electrolytic device, a boiler water system, a distiller, a water softening system, and a membrane system.

20. The apparatus of claim 1 wherein said coating comprises at least one property selected from the list consisting of optically transparent, chemically resistant, chemically inert, electrolytically active, metallic, and a combination thereof.

21. The apparatus of claim 1 wherein said coating comprises a titanium coating.

22. The apparatus of claim 1 wherein said coating comprises a diamond coating.

23. The apparatus of claim 1 wherein one of said optical windows comprises an anode.

24. The apparatus of claim 23 further comprising a power supply providing a positive electrical potential to said anode and a negative electrical potential to said cathode.

25. The apparatus of claim 24 wherein an electrical polarity of said anode and said cathode is reversible.

26. The apparatus of claim 25 wherein reversing said polarity cleans a surface of said cathode.

27. The apparatus of claim 25 wherein reversing said polarity dissolves the scale formation.

28. The apparatus of claim 1 further comprising an anode.

29. The apparatus of claim 28 wherein said anode comprises a dimensionally stable anode.

30. The apparatus of claim 28 wherein said optical windows comprise cathodes.

31. The apparatus of claim 30 further comprising a reversible power supply providing a positive electrical potential to said anode and a negative electrical potential to said cathode.

32. A method for detecting scale formation, the method comprising the steps of:
shining an energy beam through a first optical window, through a fluid stream, and through a second optical window, the windows comprising an electrically conductive coating and at least one window functioning as a cathode;
detecting an intensity of the energy beam; and
correlating the intensity with an amount of scale formation on at least one of the optical windows, thereby measuring the amount of scale formation.

33. The method of claim 32 wherein the energy beam comprises infrared energy.

34. The method of claim 32 further comprising the step of determining a concentration of carbonate in the fluid stream.

35. The method of claim 34 wherein the determining step comprises measuring a rate of change of the intensity.

36. The method of claim 32 further comprising the step of activating a control system when a predetermined amount of scale formation is detected.

37. The method of claim 36 further comprising the step of alerting an operator.

38. The method of claim 36 further comprising the step of stopping operation of a system.

39. The method of claim 38 further comprising the step of cleaning the system.

40. The method of claim 36 further comprising the step of initiating regeneration of ion exchange resin in a water softening system.

41. The method of claim 32 further comprising the steps of applying a positive electrical potential to one of the optical windows and applying a negative electrical potential to the other optical window.

42. The method of claim 41 further comprising the step of dissolving scale on at least one of the optical windows.

43. The method of claim 42 wherein the dissolving step comprises the step of reversing the polarity of the optical windows.

44. The method of claim 42 wherein the dissolving step comprising flushing the at least one optical window with an acid.

45. The method of claim 32 comprising the step of providing an anode.

46. The method of claim 45 wherein the anode comprises a third coated optical window.

47. The method of claim 45 wherein the anode comprises a dimensionally stable anode.

48. The method of claim 45 further comprising the step of applying a positive electrical potential to the anode and applying a negative electrical potential to the first and second optical windows.

49. The method of claim 48 further comprising the step of cleaning the first and second optical windows.

50. The method of claim 49 wherein the cleaning step comprises applying a negative electrical potential to the anode and applying a positive electrical potential to the first and second optical windows.

* * * * *